US010914738B2

(12) United States Patent
Bruderer et al.

(10) Patent No.: US 10,914,738 B2
(45) Date of Patent: Feb. 9, 2021

(54) SUBTRACTIVE IMMUNOASSAY METHOD AND LATERAL FLOW IMMUNOCHROMATOGRAPHY ASSAY STRIP FOR PERFORMING THE METHOD

(71) Applicants: Thomas Bruderer, Basel (CH); Madhavi Muranjan, Mumbai (IN)

(72) Inventors: Thomas Bruderer, Basel (CH); Madhavi Muranjan, Mumbai (IN)

(*) Notice: Subject to any disclaimer, the term of this patent is extended or adjusted under 35 U.S.C. 154(b) by 119 days.

(21) Appl. No.: 15/770,249

(22) PCT Filed: Oct. 24, 2016

(86) PCT No.: PCT/EP2016/075566
§ 371 (c)(1),
(2) Date: Apr. 23, 2018

(87) PCT Pub. No.: WO2017/072078
PCT Pub. Date: May 4, 2017

(65) Prior Publication Data
US 2018/0321238 A1 Nov. 8, 2018

(30) Foreign Application Priority Data
Oct. 29, 2015 (CH) ..................... 1579/15

(51) Int. Cl.
G01N 33/558 (2006.01)
C07K 16/12 (2006.01)
(Continued)

(52) U.S. Cl.
CPC .......... *G01N 33/558* (2013.01); *B01L 3/5023* (2013.01); *C07K 16/00* (2013.01);
(Continued)

(58) Field of Classification Search
USPC ..... 422/400, 401, 420, 425, 430; 435/287.7, 435/287.9, 970, 805, 810, 7.33; 436/169,
(Continued)

(56) References Cited

U.S. PATENT DOCUMENTS 8,679,812 B2    3/2014  Shiga
9,372,191 B2*   6/2016  Joanis .............. G01N 33/56944
(Continued)

FOREIGN PATENT DOCUMENTS

EP    1933146 A1    6/2008
EP    1970706 A1    9/2008
(Continued)

OTHER PUBLICATIONS

International Preliminary Report on Patentability dated May 1, 2018 with Written Opinion for PCT/EP2016/075566 filed Oct. 24, 2016 (English translation).
(Continued)

Primary Examiner — Christopher L Chin
(74) Attorney, Agent, or Firm — Paul D. Bianco; Katharine Davis; Fleit Intellectual Property Law

(57) ABSTRACT

A subtractive immunoassay for detecting the presence or absence of first and second analytes in a sample includes in the following order the steps of: a) conjugating a first detector antibody to the first analyte to tag the first analyte with a first detector tag; b) conjugating a first capture antibody to the first analyte to capture the first analyte to completely deplete the first analyte from the sample; c) conjugating a second detector antibody to the second analyte in the depleted sample to tag the second analyte with a second detector tag; d) conjugating a second capture antibody to the second analyte to capture the second analyte from the sample; e) detecting presence or absence of the first and second detector tags at the site of the first and second
(Continued)

capture antibody, respectively, and thereby detecting the presence or absence of the first and second analytes in the sample.

19 Claims, 1 Drawing Sheet

(51) Int. Cl.
    *C07K 16/00*     (2006.01)
    *G01N 33/569*     (2006.01)
    *B01L 3/00*     (2006.01)
    *G01N 33/52*     (2006.01)

(52) U.S. Cl.
    CPC ......... *C07K 16/1271* (2013.01); *G01N 33/52* (2013.01); *G01N 33/56938* (2013.01); *Y10T 436/25375* (2015.01)

(58) Field of Classification Search
    USPC .............................. 436/514, 518, 530, 810
    See application file for complete search history.

(56) References Cited

U.S. PATENT DOCUMENTS

| | | | |
|---|---|---|---|
| 2008/0206889 A1* | 8/2008 | Harris | G01N 33/54313 436/518 |
| 2012/0295812 A1 | 11/2012 | Shiga | |
| 2015/0285799 A1 | 10/2015 | Esfandiari | |

FOREIGN PATENT DOCUMENTS

| | | |
|---|---|---|
| WO | 2005031356 A1 | 4/2005 |
| WO | 2009123667 A2 | 10/2009 |
| WO | 2010104245 A1 | 9/2010 |

OTHER PUBLICATIONS

Mertz. Exclusive *Staphylococcus* throat carriage—at risk populations. Arch Intern Med, 169 (2009), pp. 172-178.
Y. Levy et al. Relation between nasal carriage of *Staphylococcus aureus* and surgical site infection in orthopedic surgery: The role of nasal contamination. A systematic literature review and meta-analysis. Orthopaedics & Traumatology: Surgery & Research. vol. 99, Issue 6, Oct. 2013, pp. 645-651.
H. Honda et al. *Staphylococcus aureus* nasal colonization and subsequent infection in intensive care unit patients: does methicillin resistance matter? Infect Control Hosp Epidemiol. Jun. 2010;31(6):584-91.
Kavanagh et al. The use of surveillance and preventative measures for methicillin-resistant *Staphylococcus aureus* infections in surgical patients. Antimicrobial Resistance and Infection Control. 2014, 3:18.
Young Py et al. Surgical site infections.Surg Clin North Am. Dec. 2014;94(6):1245-64.
Bode et al. 2010 Preventing Surgical-Site Infections in Nasal Carriers of *Staphylococcus aureus* N. Engl. J. Med. 362 (1) 9-17.
Yamada K et al., Detection of Methicillin-Resistant *Staphylococcus aureus* Using a Specific Anti-PBP2a Chicken IgY Antibody. Jpn. J. Infect. Dis., 66, 103-108, 2013.
Rina Smolina, Nancy S Miller, and Maxim D Frank-Kamenetskii. Artif DNA PNA XNA. Oct.-Dec. 2010; 1(2): 76-82. doi: 10.4161/ adna.1.2.13256 PMCID: PMC3116573 PNA-based microbial pathogen identification and resistance marker detection. An accurate, isothermal rapid assay based on genome-specific features.
Lawrence Y. L. Lee, Magnus Hook, David Haviland, Rick A. Wetsel, Edward O. Yonter, Peter Syribeys, John Vernachio, and Eric L. Brown. Inhibition of Complement Activation by a Secreted *Staphylococcus aureus* Protein. The Journal of Infectious Diseases 2004; 190:571-9.

Brian F. King and Brian J. Wilkinson. Binding of Human Immunoglobulin G to Protein A in Encapsulated *Staphylococcus aureus*. Infection and Immunity, 1981; 33 (3):666-672.
Daniel Lim and Natalie C.. Strynadka. Structural basis for the beta-lactam resistance of PBP2a from methicillin-resistant *Staphylococcus aureus*. Nature structural biology, 2002; 9 (11):870-876.
Dirk-Jan Scheffers and Mariana G. Pinho. Bacterial Cell Wall Synthesis: New Insights from Localization Studies. Microbiology and Molecular Biology Reviews 2005; 69 (4):585-607.
Mariana G. Pinho, Herminia de Lencastre, and Alexander Tomasz. An acquired and a native penicillin-binding protein cooperate in building the cell wall of drug-resistant staphylococci. PNAS 2001; 98 (19) 10886-10891.
Hidehito Matsui, Hideaki Hanaki, Megumi Inoue, Hiroyuki Akama, Taiji Nakae, Keisuke Sunakawa, and Satoshi Omura.Development of an Immunochromatographic Strip for Simple Detection of Penicillin-Binding Protein 2'. Clinical and Vaccine Immunology 2011; 18(2):248-253.
Mariana G. Pinho and Jeff Errington. Recruitment of penicillin-binding protein PBP2 to the division site of *Staphylococcus aureus* is dependent on its transpeptidation substrates. Molecular Microbiology 2005; 55 (3) 799-807.
Mariana G. Pinho and Jeff Errington. Dispersed mode of *Staphylococcus aureus* cell wall synthesis in the absence of the division machinery. Molecular Microbiology 2003; 50(3):871-881.
Paper based point-of-care testing disc for multiplex whole cell bacteria analysis (Using the immuno-disc, the presence of *Staphylococcus aureus* and P. aeruginosa can be identified by the color change in the testing region within 5 min of sample application onto the disc.). Chen-zhong Li, Katherine Vandenberga, Shradha Prabhulkara, Xuena Zhua, Lisa Schneperb, Kalai Metheeb, Charles J. Rosserd, Eugenio Almeidec. Biosensors and Bioelectronics 2011; 26:4342-4348.
Parul A. Patel, Nathan A. Ledeboer, Christine C. Ginocchio, Susan Condon, Stephanie Bouchard, Peibing Qin, Tobi Karchmer, and Lance R. Peterson. Performance of the BD GeneOhm MRSA Achromopeptidase Assay for Real-Time PCR Detection of Methicillin-Resistant *Staphylococcus aureus* in Nasal Specimens. J Clin Microbiol 2011 49(6):2266-2268.
Gleb Pishchany, Susan E. Dickey, and Eric P. Skaar . Transport Components IsdA and IsdB Infection and Immunity 2009; 77(7):2624-2634.
Santhana Raj L., Hing H. L., Baharudin Omar, Teh Hamidah Z., Aida Suhana R., Nor Asiha C.P., Vimala B., Paramsarvaran S., Sumarni G. and Hanjeet K. Rapid Method for Transmission Electron Microscope Study of *Staphylococcus aureus* ATCC 25923. Annals of Microscopy 2007; 7:102.
D.A. Mecarthy, Marion G. Macey, Mary R. Cahill, and A.C. Newland. Effect of Fixation on Quantification of the Expression of Leucocyte Function-Associated Surface Antigens. Cytometry 1994; 17:39-49.
Daniel Pirici, Laurentiu Mogoanta, Samir Kumar-Singh, Ionica Pirici, Claudiu Margaritescu, Cristina Simionescu, and Radu Stanescu. Journal of Histochemistry & Cytochemistry. Antibody Elution Method for Multiple Immunohistochemistry on Primary Antibodies Raised in the Same Species and of the Same Subtype. 2009; 57 (6):567-575.
Baochong Gao, Theresa M. Curtis, Frank A. Blumenstock, Fred L. Minnear and Thomas M. Saba. Increased recycling of a5b1 integrins by lung endothelial cells in response to tumor necrosis factor. Journal of Cell Science, 2000; (113):247-257.
Geraint J. Parfitt, Yilu Xie, Korey M. Reid, Xavier Dervillez, Donald J. Brown, James V. Jester. A Novel Immunofluorescent Computed Tomography (ICT) Method to Localise and Quantify Multiple Antigens in Large Tissue Volumes at High Resolution. PLOS ONE 2012; 7(12 ):e53245.
Eric L. Brown, Yasuhiro Nishiyama, Jesse W. Dunkle, Shreya Aggarwal, Stephanie Planque, Kenji Watanabe, Keri Csencsits-Smith, M. Gabriela Bowden, Sheldon L. Kaplan, and Sudhir Paul. Constitutive Production of Catalytic Antibodies to a *Staphylococcus aureus* Virulence Factor and Effect of Infection. Journal of Biological Chemistry 2012; 287(13):9940-9951.

(56) References Cited

OTHER PUBLICATIONS http://www.did.it/contenuti/Ibm/biblio/Evaluation%20of%20ESwab%20for%20maintaining%20viability%20of%20anaerobe.pdf.

Poetz, Sequential Multiplex Alalyte Capturing for Phosphoprotein Profiling, Molecular & Cellular Proteomics, vol. 9, No. 11, Nov. 1, 2010, p. 2474-2481.

Kazuki, Discrimination of methicillin-resistant *Staphylococcus aureus* from methicillin-susceptible . . . , Journal of Immuological Methods, vol. 388, No. 1-2, 2013, p. 40-45.

Keiko, Detection of Methicillin-Resistant *Staphylococcus aureus* using specific anti-PBP2a chicken IgY antibody, Japanese J of Infectious Diseases, vol. 66, No. 2, 2013, p. 103-108.

International Search Report dated Nov. 28, 2016 for PCT/EP2016/075566 filed Oct. 24, 2016.

Written Opinion for PCT/EP2016/075566 filed Oct. 24, 2016.

\* cited by examiner

SUBTRACTIVE IMMUNOASSAY METHOD AND LATERAL FLOW IMMUNOCHROMATOGRAPHY ASSAY STRIP FOR PERFORMING THE METHOD

TECHNICAL FIELD

The invention is directed to a method for detecting the presence or absence of a first analyte and of a second analyte in a sample, the method comprising an immunoassay. It further refers to a lateral flow immunochromatography strip for performing the immunoassay and a kit for detecting the presence or absence of a first analyte and of a second analyte using said method.

PRIOR ART

Many nosocomial infections, including post-surgical wound infections are due to nasopharyngeal colonization by *Staphylococcus aureus* (*S. aureus*). The rate of nasal colonization is very high, with one in three patients being positive (Ref 1, Ref 2, Ref 3). Post-operative infection and colonization can be prevented with pre-operative detection of *S. aureus* and antibiotic treatment. Current screening methods to analyze nasal samples for antibiotic resistance take a relatively long time to deliver results. Often physicians have to make treatment decisions without the results, resulting in high risk of use of ineffective and broad spectrum antibiotics, or overuse of antibiotics, and failure to decolonize. Therefore a rapid test to screen *S. aureus* in nasal samples is an urgent need in the surgical setting (Ref 4, Ref 5, Ref 6).

So far multiple assays for detection of *S. aureus* are available. These tests are mainly antibody- or PCR-based. Also new techniques are being developed with specialized reagents like aptamers. These tests allow identification of *S. aureus*, and further identification of methicillin-resistant *Staphylococcus aureus* (MRSA), or methicillin-susceptible *Staphylococcus aureus* (MSSA) i.e. the tests are engineered to detect MRSA from a uniform MRSA population, or a mixed MRSA and MSSA population; as well as to detect MSSA from a uniform MSSA population.

However, the only definite distinction between MRSA and MSSA is the presence of penicillin binding protein 2a (PBP2a) and its encoding gene mec A which is found in MRSA, all other components being common to both. There is no unique antigen/epitope in MSSA. Hence there is no antibody unique to MSSA that will not bind MRSA. This problem of having a unique antigen/epitope only for a first analyte (e.g. MRSA) but not for a second analyte (e.g. MSSA) exists for other bacteria as well. Examples may be the detection of other antibiotic resistant bacteria, e.g. tetracycline resistance or highly relevant carbapenemases (e.g. NDM, KPC-2) and extended-spectrum β-lactamases (ESBL), from a potentially mixed population of antibiotic-sensitive and antibiotic-resistant bacteria of a single strain; detection of Gram negative bacterial pathogens from a potentially mixed population of pathogenic and non-pathogenic bacteria of a single strain, e.g. via the type III secretion system (TTSS) or the pyelonephritis associated pili (p-fimbriae) of uropathogenic *Escherichia coli* (*E. coli*).

Differences in *S. aureus* Protein A gene (spa) typing and nucleotide based polymorphisms exist between MRSA and MSSA, but these are not always exclusive, and extensive variations in spa gene make them difficult to use for routine analysis of MRSA and MSSA.

Thus no point of care test exists for simultaneously identifying MRSA and MSSA in a mixed population of MRSA and MSSA strains. Currently this is possible only by antibody or aptamer based staining of the mixed population using distinct tags e.g. two different fluorochrome tags for PBP2a and PBP2, followed by visual inspection under the microscope to demarcate cells with both tags i.e. MRSA, vs. a single tag i.e. MSSA.

A strip-based immunochromatographic detection (also called lateral flow immunochromatography) of MRSA is known e.g. from EP1970706, either by detecting free PBP2a protein (after extraction) (Ref 14) or in whole cells (Ref 7). U.S. Pat. No. 8,679,812 describes a 2-D antibody array for evaluating multiple antigens or proteins including PBP2 and PBP2a antigens by extracting the antigens from the cells. However, all these detection assays do not allow simultaneous detection of MRSA and MSSA in a mixed *S. aureus* population.

Other methods such as PCR of specific encoding genes, or biochemical tests that detect both MRSA and MSSA are known. However, these tests do not serve as point of care (POC) diagnosis as sophisticated lab equipment is required. Also they take several hours or days to deliver the result.

There is also a fluorochrome-tagged nucleic acid hybridization method known that detects MRSA as double positive for the PBP2 and PBP2a encoding genes and MSSA as single positive for PBP2 encoding gene (Ref 8). This test requires a fluorescent microscope and a digital camera in a dark room—again not applicable to point of care.

Most of these known methods also require culturing of the *S. aureus* from the patient sample prior to performing the assay. This requires many hours, often overnight.

Overall, there exists a need for rapidly identifying both MRSA and MSSA in a mixed population of *S. aureus*—commonly reported in nasal colonization—suitable for a point of care diagnosis.

SUMMARY OF THE INVENTION

It is an objective of the invention to provide an immunoassay for rapid and simultaneous detection of two analytes (e.g. MRSA and MSSA) in a sample, also in the case where only for one of them (e.g. MRSA) a unique antigen/epitope exists such that the second analyte cannot be easily distinguished in the presence of the first analyte.

Another objective of the invention is to provide a method for rapid isolation and enrichment of *S. aureus* from a sample collected directly from a biological, environmental or food specimen.

At least one of the objectives is achieved by a method according to claim 1, a lateral flow immunochromatography assay strip according to claim 8 and a kit according to claim 12. Thus, a method for detecting the presence or absence of a first analyte and of a second analyte in a sample comprises an immunoassay including in the following order the steps of: (a) conjugating a first detector antibody to the first analyte in order to tag the first analyte with a first detector tag; (b) conjugating a first capture antibody to the first analyte in order to capture the first analyte and to completely deplete the first analyte from the sample; (c) conjugating a second detector antibody to the second analyte in the depleted sample in order to tag the second analyte with a second detector tag; (d) conjugating a second capture antibody to the second analyte in order to capture the second analyte from the sample; (e) detecting the presence or absence of the first and second detector tag at the site of the first and second capture antibody, respectively, and thereby detecting the presence or absence of the first analyte and of the second analyte in the sample. The first detector antibody and the first capture antibody are specific for distinct epitopes of the first analyte; and the second detector antibody and the second capture antibody are specific for distinct epitopes of the second analyte. The first and second detector antibodies may be free first and second detector antibodies free to move in or with the sample, and the first and second capture antibodies may be immobilized first and second capture antibodies immobilized at a predefined site on a substrate.

In other words, the immunoassay of the invention—also named subtractive immunoassay—works as follows: In a first step the sample is contacted with a free first detector antibody specific to a first detector epitope of the first analyte, the first detector antibody being labelled with a first detector tag (e.g. AuNp). If the first analyte is present in sample it will conjugate with the first detector antibody and thereby is marked with the first detector tag. In a second step a immobilized first capture antibody is used to conjugate with a first capture epitope of the first analyte, the first capture epitope being distinct from the first detector epitope. Thereby, the first analyte—if present in the sample—conjugated to the first detector antibody is immobilized at the site of the first capture antibody and can be completely depleted from the sample. The presence or absence of the first detection tag conjugated to the first analyte can subsequently be detected at the immobilization site of the first capture antibody in order to determine presence or absence of the first analyte. In a third step the sample depleted of the first analyte is contacted with a free second detector antibody specific to a second detector epitope of the second analyte, the second detector antibody being labelled with a second detector tag (e.g. AuNp). If the second analyte is present in sample it will conjugate with the second detector antibody and thereby is marked with the second detector tag. In a fourth step an immobilized second capture antibody is used to conjugate with a second capture epitope of the second analyte, the second capture epitope being distinct from the second detector epitope. Thereby, the second analyte—if present in the sample—conjugated to the second detector antibody is immobilized at the site of the second capture antibody. The presence or absence of the second detector tag conjugated to the second analyte can subsequently be detected at the immobilization site of the second capture antibody in order to determine presence or absence of the second analyte.

The subtractive immunoassay is suitable for the detection of e.g. MRSA and MSSA in a point of care manner. It is rapid, simple and detection by naked eye may be possible.

The subtractive immunoassay is suitable to identify a sub-population of cells with "extra" antigens/epitopes and a sub-population of identical cells without the "extra" molecules within a mixed population (i.e. latter sub-population of cells shares all antigens/epitopes with the former, only lacks the "extra" antigens/epitopes). Examples are: the detection of post-translational protein modification variants (e.g. glycosylation, phosphorylation, S-nitrosylation, N-acetylation, methylation, lipidation, proteolysis) in a protein sample; the detection of other antibiotic resistant bacteria, e.g. tetracycline resistance or highly relevant carbapenemases (e.g. NDM, KPC-2) and extended-spectrum β-lactamases (ESBL), from a potentially mixed population of antibiotic-sensitive and antibiotic-resistant bacteria of a single strain; detection of Gram negative bacterial pathogens from a potentially mixed population of pathogenic and non-pathogenic bacteria of a single strain, e.g. via the type III secretion system (TTSS) or the pyelonephritis associated pili (p-fimbriae) of uropathogenic $E.\ coli$.

In general the amount of first capture antibody is adjusted to fully deplete the first analyte from the sample. The amount depends on the nature of the first analyte and/or second analyte. In some embodiments the concentration of the first capture antibody may be equal or higher than the concentration of the first detector antibody, preferably at a ratio between 1:1 and 5:1, more preferably between 1.5:1 and 3:1. Using slightly more capture antibody than detector antibody will ensure that all detector-antibody tagged first analyte is depleted from the sample by the first capture antibody.

In some embodiments of the invention the subtractive immunoassay may be a lateral flow immunochromatography assay, using a lateral flow assay strip comprising in sample flow direction a sample application pad, a first conjugation pad, a nitrocellulose membrane with at least one first test line and optionally at least one first control line, a second conjugation pad, a nitrocellulose membrane with at least one second test line and optionally at least one second control line, and an absorption pad; the first conjugation pad containing the first detector antibody, the first test line formed by the first capture antibody, the second conjugation pad containing the second detector antibody, and the second test line formed by the second capture antibody. The optional at least one first control line contains a first control antibody which specifically binds the first detector antibody. The optional at least one second control line contains a second control antibody, which specifically binds the second detector antibody.

In some embodiments of the invention the assay strip may comprise two or more first test lines in sequence, to ensure all first analyte is removed/depleted from the sample before it moves to the second conjugation pad.

In some embodiments of the invention at least one further set of first conjugation zone and first test line may follow the first set of first conjugation zone and first test line. With the further set of first conjugation zone and first test line so far undetected free first analyte due to a possible and not desired saturation of the first detector antibody with first analyte in the first conjugation zone can be detected. If no saturation of the first detector antibody with first analyte occurs and all first analyte is depleted within the first test line(s) (no saturation of first capture antibody) of the first set, then the first test line of the further set of first conjugation zone and first test line will be negative. If the first test line of the further set is positive, either the first detector antibody or the first capture antibody is saturated with first analyte and the assay should be repeated with a diluted patient sample. A first control line may follow the at least one further set of first conjugation zone and first test line.

In some embodiments of the invention the first analyte is methicillin-resistant $S.\ aureus$ (MRSA) and the second analyte is methicillin-susceptible $S.\ aureus$ (MSSA).

In some embodiments of the invention the first detector antibody and the first capture antibody are specific for distinct epitopes of penicillin binding protein 2a (PBP2a); and the second detector antibody and the second capture antibody are specific for distinct epitopes of penicillin binding protein 2 (PBP2).

MRSA detection via PBP2a is facile, but in a mixed population of $S.\ aureus$ MSSA detection is not possible since both MRSA and MSSA contain PBP2 (and all markers published for MSSA). The principle of the subtractive immunoassay described here is that following MRSA detection, all PBP2 associated with MRSA will be depleted in the first part of the immunoassay, allowing consecutive detection of PBP2 associated with only MSSA. Both steps are performed with a single immunochromatography assay strip.

In some embodiments of the invention the sample is collected from a biological, environmental or food specimen. The collection may be performed with a nasal swab e.g. an ESwab from Copan Diagnostics Inc.

In some embodiments of the invention the eluate from the nasal swab may be tested for the presence of S. aureus using an Ebf immunochromatography dipstick. The highly conserved nature and constitutive expression in pathogenic/invasive S. aureus of Ebf makes it a suitable marker for detection of the pathogen. Its secretion into the extracellular medium makes it readily amenable for immunochromatographic assay (ICA) lateral flow detection, without any processing of the bacteria and without any loss of the bacteria.

In an embodiment of the method to simultaneously detect MRSA and MSSA in a mixed population in point of care manner, an Ebf immunochromatography dipstick may be inserted into the nasal swab eluate taken from a patient, and read once red color develops in the test zone indicating positive for presence of S. aureus. Next, bacterial concentration may be determined using the handheld colorimetric device. Once S. aureus is detected, it may be captured on protein L-conjugated superparamagnetic beads, and tested for MRSA and MSSA on the PBP2a/PBP immunochromatography strip. The MRSA will be first detected and depleted from the sample liquid in the PBP2a test/capture line of the strip. The test line actually reads only the number of analyte particles that initially solubilized the detection antibody in the conjugate pad and carried the detection agent to the test line. The test line does not detect the number of analyte particles absorbed onto the sample pad. Hence it is very important to assay the sample below the saturation of the detection antibody in the conjugate pad. Under these conditions, after passing the test line, the sample running forward will not contain the MRSA cells, but only the MSSA cells. A second conjugation pad containing tagged anti-PBP2 detector antibody (e.g. AuNp-tagged) is positioned on the strip to receive the MSSA cells, and any MSSA-anti-PBP2-AuNp complex will be detected as a red line (if AuNp tag is used) at the PBP2 test line, and further quantified by colorimetry.

To increase sensitivity of the detection method, in some embodiments of the invention the eluate from the nasal swab or any other sample may be subjected to an isolation and enrichment step of S. aureus by using magnetic or paramagnetic beads. The step is performed before the actual subtractive immunoassay. Therefore, magnetic or paramagnetic beads may be coated with an Ig G antibody, the Ig G antibody being bound with its Fab region to the bead leaving its Fc region free to specifically interact with protein A of S. aureus.

The isolation is an enrichment step based on the natural affinity of protein A for Ig G antibodies. Protein A is expressed on the surface S. aureus and is accessible and bound by Fc region of an Ig G molecule, even in the case of encapsulated S. aureus, with very high affinity. The kinetics of binding are very rapid (Ref 10). Preferably, the Ig G is a human Ig G, because it shows the strongest binding by protein A. In a given sample, e.g. a nasal swab eluate, any S. aureus will be caught by the Fc portion of the Ig G antibody.

Pre-blocked, protein L conjugated magnetic or paramagnetic beads may be used, wherein the protein L is chemically cross-linked to the beads. An Ig G antibody may be conjugated to the magnetic bead via its Fab region and protein L. The Ig G antibody is subsequently cross-linked to protein L on the bead to avoid leaching in later steps.

It is understood, that the method for isolating and enriching S. aureus in a given sample may be a separate invention independent of the further use of the treated sample. The method for isolating and enriching S. aureus in a sample, e.g. a sample collected from a biological, environmental or food specimen, uses Ig G antibody coated beads, preferably magnetic beads, said Ig G antibody being bound with its Fab region to the beads leaving its Fc region free to specifically interact with protein A of S. aureus.

A lateral flow immunochromatography assay (ICA) paper strip may be employed for detection of the S. aureus specific marker PBP2 and the MRSA specific marker PBP2a. In a reported study, ICA has been able to detect 1 ng of PBP2a by naked eye (Ref 14). In another study whole cells of S. aureus were detected by naked eye from 500-5000 CFU/ml (Ref 17).

The method for isolating and enriching S. aureus using IgG-conjugated magnetic or paramagnetic beads may enhance the sensitivity of the subsequent immunoassay to <500 CFU/ml with respect to the clinical sample before enrichment.

In some of the embodiments a colorimeter, preferably a handheld colorimeter, may be used for quantitative analysis of MRSA and MSSA.

The invention further relates to a lateral flow immunochromatography assay strip for performing the subtractive immunoassay in order to detect a first analyte and a second analyte, the strip comprising in sample flow direction a sample application pad, a first conjugation pad, a nitrocellulose membrane with at least one first test line and optionally at least one first control line, a second conjugation pad, a nitrocellulose membrane with at least one second test line and optionally at least one second control line, and an absorption pad. The first conjugation pad contains a first detector antibody to the first analyte in order to tag the first analyte with a first detector tag. The first test line is formed by a first capture antibody to the first analyte in order to capture the first analyte and to completely deplete the first analyte from the sample. The second conjugation pad contains a second detector antibody to the second analyte in the depleted sample in order to tag the second analyte with a second detector tag. The second test line is formed by a second capture antibody to the second analyte in order to capture the second analyte from the sample. The optional at least one first control line contains a first control antibody which specifically binds the first detector antibody. The optional at least one second control line contains a second control antibody, which specifically binds the second detector antibody.

In some embodiments of the invention the first and second detector antibodies are free first and second detector antibodies free to move in or with the sample, and the first and second capture antibodies are immobilized first and second capture antibodies immobilized at the site of the first and second test line, and wherein the antibodies of the optional first and second control lines are immobilized at the site of the first and second control line.

In some embodiments of the invention the assay strip may comprise two or more first test lines in sequence, to ensure all first analyte is removed/depleted from the sample before it moves to the second conjugation pad.

In some embodiments of the invention the assay strip may comprise at least one further set of first conjugation zone and first test line following the first set of first conjugation zone and first test line. With the further set of first conjugation zone and first test line so far undetected free first analyte due to a possible and not desired saturation of the first detector antibody with first analyte in the first conjugation zone can be detected. If no saturation of the first detector antibody with first analyte occurs and all first analyte is depleted within the first test line(s) (no saturation of first capture antibody) of the first set, then the first test line of the further set of first conjugation zone and first test line will be negative. If the first test line of the further set is positive, either the first detector antibody or the first capture antibody is saturated with first analyte and the assay should be repeated with a diluted patient sample. A first control line may follow the at least one further set of first conjugation zone and first test line.

In some of the embodiments of the invention the first analyte is methicillin-resistant *Staphylococcus aureus* (MRSA) and the second analyte is methicillin-susceptible *Staphylococcus aureus* (MSSA).

In order to prevent steric hindrance, the first detector antibody and the first capture antibody may be specific for distinct epitopes of penicillin binding protein 2a (PBP2a); and the second detector antibody and the second capture antibody may be specific for distinct epitopes of penicillin binding protein 2 (PBP2).

The invention further relates to a kit comprising a lateral flow immunochromatography strip for detecting the presence or absence of a first analyte and of a second analyte in a sample as described above. The kit may further comprise at least one of the following: (i) a swab for taking a sample from a patient, including agents to elute the sample from the swab; (ii) an Ebf immunochromatography dipstick to detect the absence or presence of *S. aureus* in a sample; (iii) Ig G antibody coated magnetic beads to isolate and enrich *S. aureus*, said Ig G antibody being bound with its Fab region to the magnetic bead leaving its Fc region free to specifically interact with protein A of *S. aureus*; including agents for washing steps and eluting *S. aureus* from the magnetic beads; and (iv) an agent for permeabilization of *S. aureus*.

The subtractive immunoassay and the kit as described in the above embodiments of the invention can be used at point of care because:

It is a simple immunochromatography assay format that does not need any instrumentation save the portable colorimeter. The only manipulations are the magnetic bead based enrichment and optional fixation and/or permeabilization of *S. aureus* in the sample, which require magnetic or paramagnetic beads, an external magnet, a pipette, a few buffers, a fixative and a permeabilizing agent. All these parts may be included in a kit to perform the immunoassay described above.

Quantification by portable colorimeter is available.

Only 50 microliter liquid is required for sampling using the immunochromatography assay, allowing the processing of a sample in a small volume preventing unnecessary dilution of samples that may have very low *S. aureus* counts (CFU—colony forming units). Enrichment of the bacteria using magnetic or paramagnetic beads is likely to enhance the sensitivity of the assay. The proposed assay is based on an immunochromatography assay format with sensitivity of 500 CFU/ml, and actually 25 CFU/strip (in 50 microliters applied to strip). Therefore the enrichment step can enhance the sensitivity of the assay to <500 CFU/ml.

The entire assay period does not exceed 1 hour. The assay time form obtaining a swab to final detection and quantification is estimated between 35 min to 54 min, with 6 minutes for washes and handling. Sample elution 1-2 min, detection of Ebf (*S. aureus*-both MRSA and MSSA) 5 min, fixation of *S. aureus* 20 min, permeabilization of the organism 1 min, capture of *S. aureus* 1-2 min, elution of *S. aureus* from capture magnet 4 min, detection of PBP2a (MRSA) and PBP2 (MSSA) 5-20 min. Total time=34 min-54 min, and handling/PBS washes should not take more than 6 minutes.

The described assay allows detection of *S. aureus* by naked eye.

Simultaneous identification of MRSA and MSSA in a mixed population is possible.

BRIEF EXPLANATION OF THE FIGURES

The invention is described in greater detail below with reference to embodiments that are illustrated in the figures. The figures show.

EMBODIMENTS OF THE INVENTION

Figure 1:
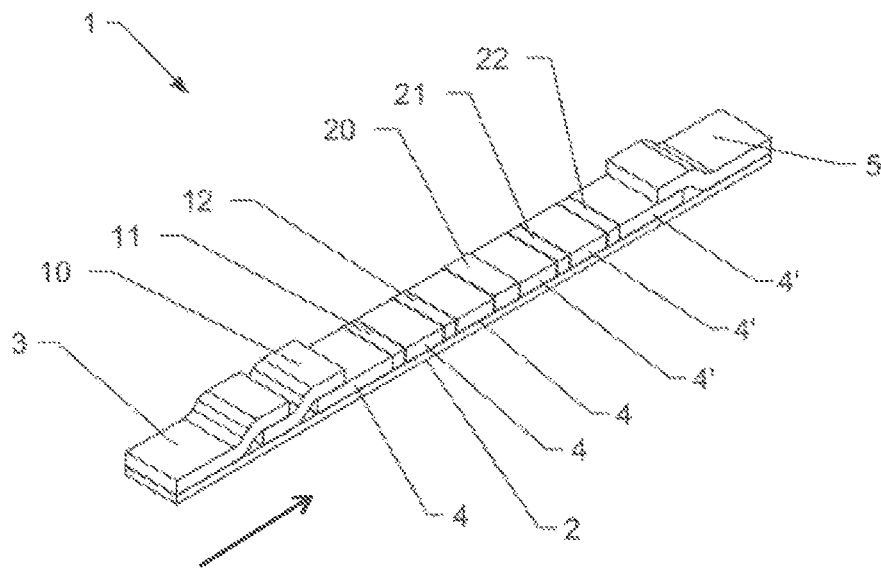
FIG. 1 a schematic drawing of a lateral flow immunochromatography assay strip.

In the following an immunoassay process is described which allows identification of *Staphylococcus aureus* (*S. aureus*) and identification of both the MRSA and MSSA strains from a nasal swab containing a mixture of both resistant and sensitive strains. It is understood that the subtractive immunoassay described in the following can also be used for other analytes different from MRSA and MSSA and can also be upscaled to more than two distinct analytes. The subtractive immunoassay is particularly useful when only for one of the two analytes a unique antigen/epitope exists which is not present in the second analyte, all other antigens/epitopes being identical.

For the immunoassay described here four markers are used: (i) extracellular factor extracellular binding factor (Ebf) for initially detecting *S. aureus* in a sample (e.g swab eluate); (ii) protein A as a specific marker for *S. aureus* identification while being used to isolate and enrich *S. aureus* from a sample, (iii) penicillin binding protein 2a (PBP2a) specific for detecting MRSA and (iv) penicillin binding protein 2 (PBP2) specific for MRSA and MSSA and used to detect MSSA. These two markers are used in the actual subtractive immunoassay.

Extracellular Binding Factor (Ebf)

Ebf (extracellular fibrinogen-binding protein) acts as an adhesin through binding to fibrinogen in extracellular matrix. It also binds to complement protein C3 which may serve to neutralize complement activation initiated by *S. aureus* during the early stages of infection, when capsule production has not been initiated (Ref 9). Ebf is chosen as an indicator for *S. aureus* due to its highly conserved nature and constitutive expression in pathogenic/invasive *S. aureus*, and because its secretion into the extracellular medium makes it readily amenable for immunochromatographic assay (ICA) lateral flow detection, without any processing of the bacteria.

Protein A

The immunoassay starts with enrichment of *S. aureus* to optimize sensitivity of MRSA and MSSA detection/quantification by exploiting the immunoglobulin binding property of protein A. Protein A is a highly conserved *S. aureus* specific marker expressed on the cell surface. Protein A binding to Ig G Fc domain shows extremely rapid binding kinetics within 20 seconds (Ref 10). Thus capture of bacteria also serves indirectly for detecting *S. aureus* protein A.

Penicillin Binding Protein 2a (PBP2a)

PBP2a and its encoding gene mec A are present only in MRSA, and are central to the methicillin resistance mechanism of these organisms. PBP2a unlike PBP2, has low affinity for beta-lactams. In conjunction with transglycosylase activity of PBP2, PBP2a transpeptidase activity permits peptidoglycan synthesis in presence of beta lactams in MRSA cells (Ref 11; Ref 12; Ref 13). PBP2a is unique to MRSA and hence is chosen for detection and selective depletion of MRSA cells from test sample. There are many immunoassasys used in literature and available commercially for PBP2a detection. A large number of monoclonal and polyclonal antibodies are available against PBP2a.

Penicillin Binding Protein 2 (PBP2)

PBP2 is a key enzyme involved in synthesis of the major cell wall component peptidoglycan, and is present in all *S. aureus* cells. The enzyme shows both transglycolase activity and the beta-lactam sensitive transpeptidase activity, unlike PBP2a that acts only as a transpeptidase. The assay described is designed to remove all MRSA cells from test sample prior to assessing presence of MSSA cells via PBP2 (subtractive immunoassay).

A condition when selecting markers is that selected markers must always be present at measurable concentrations on or in *S. aureus* bacteria colonizing the nasopharyngeal mucosa, or colonized mucosa. Ebf, protein A, and PBP2 are always present and hence measurable in all *S. aureus* (MRSA and MSSA) while PBP2a is always present and can be measured in MRSA strains. All these proteins have been studied in published literature (Ref 9; Ref 10; Ref 14; Ref 15; Ref 16).

Sampling Process

Copan Diagnostics Inc.'s ESwab is a validated swab (CLSI M40-A performance standard; Quality Control of Microbiological Transport Systems) for collection and transport of clinical specimens containing aerobes, and anaerobes. The swab maintains viability of aerobes and anaerobes for up to 48 hours at both refrigerator (4-8° C.) and room temperature (20-25° C.). ESwab will be used to collect the patient's sample which is automatically eluted for 1-2 min (no vortexing needed for Eswab) (Ref 18) from the swab into 1 ml PBS. The swab eluate can be transferred with a pipette to a fresh tube. Other swab systems may be used. However, the mentioned ESwab gave nearly 1 log (base 10) higher counts for microbes studied compared to other swabs (Ref 26).

The following sections detail detection of Ebf, capture of *S. aureus* via protein A, detection of PBP2a and PBP2 (subtractive immunoassay), construction and mechanism of the ICA strip, the portable colorimetric device in that order. The experiments for assay performance with respect to sensitivity of the assay (100 CFU/sample) and assay specificity are described.

Detection, Fixation, Enrichment and Permeabilization of *S. aureus*

An Ebf immunochromatography dipstick will be inserted into the swab eluate, and read once red color develops in the test zone indicating presence of *S. aureus*. Following a positive readout for Ebf, the bacteria in the eluate will be fixed with an equal volume of 2.7% paraformaldehyde and 0.005% glutaraldehyde in PBS for 20 min (the average doubling time of *S. aureus*) (Ref 16; Ref 19; Ref 20). The liquid volume will be increased 30 fold with PBS to dilute the fixatives to final concentration of 0.045% formaldehyde, 0.0008% gluteraldehyde. At these strengths no fixation is likely since 0.4% formaldehyde needs 4 min at 37° C. to cross-link (Ref 21).

The fixatives must be diluted sufficiently to allow protein L to bind Ig G and to prevent fixation of the Ig G in the next step. Subsequently the beads will be stripped to release *S. aureus* from the immobilized antibody. As fixed antibody may not be stripped efficiently, preventing protein L (on bead) and antibody from fixing is important.

Protein L binds mouse immunoglobulin kappa I light chain only, leaving the Fc domain free. Ig G will be allowed to bind to protein L-beads. Once Ig G binds to protein L it will be chemically crosslinked, to prevent it from co-eluting with *S. aureus* in subsequent stripping. The Ig G1 coated, pre-blocked Protein L-conjugated superparamagnetic beads will be added to swab eluate. The Fc domain of the Ig G is free to interact with protein A of *S. aureus*. Addition of these beads will result in the free Fc domain of Ig G1 on the bead binding to cell surface expressed protein A on *S. aureus*. Due to extremely rapid binding kinetics (within 20 seconds (Ref 10)) of protein A to Fc domain of Ig G, *S. aureus* can be efficiently isolated and enriched in a point of care manner. After 1-2 min binding, *S. aureus* may be further processed.

A strong external magnet may be used to settle and restrain the beads while washes and fluid changes are done. Supernatant fluid will be removed carefully by pipette during washes or fluid changes. The *S. aureus* on the beads will be washed twice with PBS, permeabilized with lysostaphin (Sigma) at a final concentration of 10-30 ng/ml for 1 min in GTE buffer (glucose 50 mM, Tris-HCl 20 mM, pH 7.5, EDTA 10 mM). The permeabilization allows antibody access and binding to the transmembrane proteins PBP2 and PBP2a (Ref 16; Ref 22). The beads will be washed twice with PBS.

Release of *S. aureus* from the Capture Beads

The *S. aureus* is enriched from swab eluate by magnetic capture for increasing the sensitivity of immunodetection. The *S. aureus* should be released from the protein L-beads for two reasons: (i) Protein L binds human immunoglobulins kappa chain and it binds kappa I chain of mouse immunoglobulin. Unless the available antibody reagents (antibodies against PBP2 and PBP2a) are kappa III or IV, or lamba type light chain-Ig Gs that do not bind protein L, presence of the protein L will cripple the immunoassay completely as it will bind the antibodies in the ICA indiscriminately; and (ii) the MRSA and MSSA cells of *S. aureus* that bind the beads in a mixed population will no longer be distinguished by the ICA, which is the main diagnostic goal of the described assay format.

The beads carrying *S. aureus* may be washed twice (2 minutes/wash) in an antibody stripping buffer (50 mM glycine, 150 mM NaCl, pH 2.5). (Ref 23; Ref 24) and neutralized with ⅒ the volume of 1 M Tris, pH 8.5. These buffers are routinely used for dissociating the antibody from the immobilized Protein A, and have been used for effectively dissociating antibody from cell surface. If stripping is incomplete, the higher strength 0.1M glycine-HCl buffer may be used.

Immunochromatographic Detection of MRSA and MSSA Via PBP2a and PBP2

Antibodies that can be employed for the ICA assays described here are listed below. These antibodies are commercially available and/or used in literature.

Anti-Ebf antibodies: Anti-Ebf mouse or human polyclonal purified IgG (Ref 25)

Anti-PBP2a antibodies: Capture mab IgM (clone 1G12) and detection mab IgG (clone 10G2) (Ref 14); Capture mab clone #M8121521 and detection mab clone #M8121522 (from Fitzgerald Industries International); Capture mab clone #M8121523 and detection mab clone #M8121522 (from Fitzgerald Industries International); Anti-PBP2a mouse monoclonal antibodies from Biosource catalog #MBS530969, MBS530221 and MBS531915 (from MyBioSource, Inc);

Anti-PBP2 antibodies: Anti-PBP2 rabbit polyclonal (Ref 16).

ICA Working Principle (Subtractive Immunochromatography Assay)

A paper based lateral flow immunochromatographic strip 1 with two conjugate pads 10, 20 is provided for consecutive detection of PBP2a followed by PBP2 in whole S. aureus cells. The strip construct is shown in FIG. 1.

The immunochromatographic strip for PBP2a/PBP2 detection (PBP2a/PBP2 strip) comprises eight parts or regions/zones listed in the following in flow direction of the sample (arrow in FIG. 1):

1.) A sample application zone 3 (sample application pad). This zone will be dipped into the sample liquid (swab eluate or eluate after enrichment of S. aureus), from where it will travel along the strip until the last zone (absorption pad).

2.) First conjugation zone 10 (first conjugate pad). This zone contains a free first detector antibody. The first detector antibody is specific to the first analyte (here PBP2a) under detection, and is conjugated to a signal generation system (first detector tag). The first detector tag may be gold nanoparticles (AuNp) for signal purpose, as it is highly sensitive and the signal is visible to the naked eye in form of a red colour developed in presence of the first analyte. The sample flows from application zone (sample application pad) to the first conjugation zone (first conjugate pad), where the first detector antibody (e.g. AuNp-tagged antibody) will bind the first analyte.

3.) First test line 11 (first capture/test zone). This zone contains an immobilized first capture antibody which is specific to the first analyte (e.g. PBP2a), but recognizes a different epitope from the first detector antibody of the first conjugate pad. The first analyte-first detector antibody complexes formed in the first conjugate pad will bind to the immobilized first capture antibody via the first analyte, concentrating the complexes in the first capture zone. The focusing of AuNp in the first test line will appear as a distinct red color visible to the naked eye, whose intensity will increase in proportion to first analyte concentration. The MRSA cells containing PBP2a will be captured and detected in the first capture zone and completely depleted from the sample.

4.) First Control line 12 (first control zone). The excess first detector antibody (e.g. AuNp-tagged), and the unbound material from the sample will migrate to the first control zone. This zone contains a first control antibody which specifically binds the first detector antibody (AuNp-conjugate). The first control zone absorbs the excess free first detector antibody, as well as serves as a confirmation that the strip device is functioning properly. A red color on first control line indicates the device is working.

5.) Second conjugation zone 20 (second conjugate pad). The unbound material including bacterial cells, now free of first detector antibody (anti-PBP2a-AuNp antibody) and first analyte (MRSA cells), will flow to the second conjugate pad. The second conjugate pad contains a free second detector antibody (e.g. anti-PBP2 antibody conjugated to AuNp) specific to the second analyte (e.g. PBP2).

6.) Second test line 21 (second capture/test zone). This zone contains an immobilized second capture antibody which is specific to the second analyte (e.g. PBP2), but recognizes a different epitope form the second detector antibody of the second conjugate pad. The second analyte-second detector antibody complexes formed in the second conjugate pad will bind to the immobilized second capture antibody via the second analyte, concentrating the complexes in the second capture zone. The focusing of AuNp in the second test line will appear as a distinct red color visible to the naked eye, whose intensity will increase in proportion to second analyte concentration. Thus MSSA cells containing PBP2 will be captured and detected here.

7.) Second Control line 22 (second control zone). The excess second detector antibody (e.g. AuNp-tagged), and the unbound material from the sample will migrate to the second control zone. This zone contains a second control antibody which specifically binds the second detector antibody (AuNp-conjugate). The second control zone absorbs the excess free second detector antibody and serves as a confirmation that the strip device is functioning properly. A red color on second control line indicates the device is working.

8.) Absorption zone 5 (absorption pad). Lastly the absorption pad will absorb superfluous sample liquid containing unreacted/unbound material.

Construction of an Immunochromatographic Strip for Subtractive Immunochromatography In the following a possible method for construction of an immunochromatographic strip is described.

The placement of the zones for the strip may be printed onto a plastic support 2. The sample application pad 3, conjugation pads 10, 20, nitrocellulose membranes 4, 4', and absorption pad 5 cut in the right size are adhered to the plastic support. The construct of the ICA strip comprises two nitrocellulose strips 4, 4' held together by conjugation pad 20. The first strip of nitrocellulose 4 will have the conjugation pad 10 at its proximal end (to end closer to the application pad 3). The second strip of nitrocellulose 4' will have the absorption pad 5 at its distal end (the end further away from the application pad 3).

The pre-construct is sterilized by UV/8 hr. The first and second test line 11, 21 and the first and second control zone 12, 22 are created by spotting the first and second capture antibody and the first and second control antibody on the respective zones on the nitrocellulose membrane 4, 4' with a BioDotter Handheld Liquid Dispenser (Biodot Inc, Irvine, Calif.) and incubated at 37° C. for 30 min. The nitrocellulose membrane will be blocked with 0.5% casein solution for 20 min, and washed (Ref 14). The blocking step prevents non-specific binding from irrelevant sample constituents when the strip is in use. 18 microliters of blocked first and second AuNp-detector antibody conjugate will be applied to the first 10 and second 20 conjugation pad respectively and dried for 2 h at 37° C. A conjugation pad can be made of glass fiber (Millipore) or cellulose. After air-drying the first conjugate pad will be placed at the proximal end of the nitrocellulose membrane. The first conjugation pad is positioned to slightly overlap both the sample application pad 3 and the nitrocellulose pad 4 (approx. 0.2 cm). The second conjugation pad 20 overlaps the nitrocellulose pads 4, 4' on both sides (approx. 0.2 cm). The completed strip will be then saturated with buffer 0.25% Triton X-100, 0.05 M Tris-HCl, and 0.15 mM NaCl (pH 7), dried and stored in a dessicator at 4° C.

20 nm to 40 nm AuNp (gold nanoparticles) are used to tag the first and second detector antibody. Other tags for visualization of captured analyte may also be used.

The AuNps of desired size are obtained by Turkevich's (1985) method for reduction of gold in an aqueous solution controlling volume of reducing/stabilizing agent. Conjugation of AuNp to antibody is performed at isoelectric point of the antibody in order to overcome the Stern layer of the AuNp to permit their binding to antibody. Gold colloid suspension and anti-PBP2a mab at final concentration 30 microg/ml are mixed and incubated for 20 min in reference (Ref 14). Then 1.0% sodium casein will be added as blocking agent. After removal of unbound Ig G at 14,000×g for 15 min the pellet is resuspended (Ref 14) in 0.5 ml of 10 mM Tris-HCl buffer containing 0.1% sodium casein (and 10% trehalose dihydrate, pH 8.2 was used) and applied to the conjugation pad.

For the first conjugation pad 10 a mouse anti-PBP2a mab (first detector antibody) is used. For the first test line 11 a mouse anti-PBP2a mab (first capture antibody) against a different epitope sufficiently far from the epitope recognized by the first detection antibody to prevent steric hindrance during binding is used. For the first control line 12 an anti-mouse antibody that recognizes the specific isotype of the first detection antibody (usually antimouse Ig G) is used. Antibodies of other sources (non-murine) may also be used as detection antibody.

For the second conjugation pad 20 a mouse anti-PBP2 mab (second detector antibody) is used. For the second test line 21 a mouse anti-PBP2 mab (second capture antibody) against a different epitope sufficiently far from the epitope recognized by the second detection antibody to prevent steric hindrance during binding is used. For the second control line 22 an anti-mouse antibody that recognizes the specific isotype of the second detection antibody (usually anti-mouse Ig G) is used.

The specificity of the assay will be higher if monoclonal antibodies are used for detection and capture of first and second analyte. The first specificity of assay binding is due to the first detector antibody; hence if only one monoclonal is available (the others available being polyclonal) it should be used for the first detection antibody as it is highly specific for the first analyte, and unlikely to cross-react.

Strip Assay Process and Readouts

The immunochromatographic strip is dipped in 50 microliter of the cell suspension (following immunomagnetic capture and release) until colour develops for the test zone(s) (depending on whether MRSA, MSSA or both are present) and for the control zone of the PBP2 detection (last control line that sample passes). The intensity of the red test line correlates positively to increasing bacterial concentrations.

The different test line will turn:
 red (positive) for PBP2a, not red (negative) for PBP2 in presence of MRSA only;
 not red (negative) for PBP2a, but red (positive) for PBP2 in presence of MSSA only; or
 red (positive) for PBP2a, and red (positive) for PBP2 in presence of both MRSA and MSSA.

The result of both test lines being negative will not occur as the sample has previously been tested for the presence of *S. aureus* (Ebf assay; enrichment via Protein A).

Figure 2:
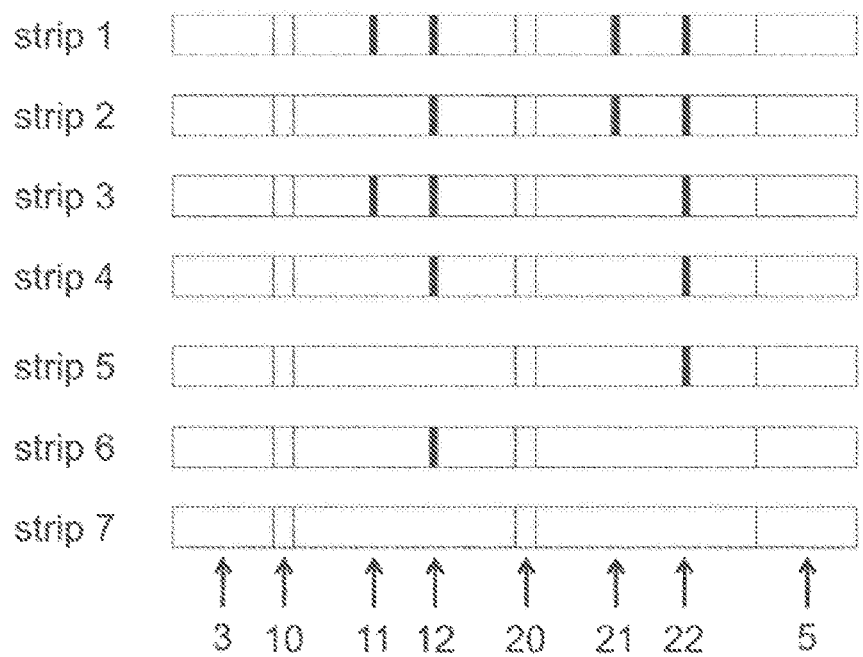
FIG. 2 possible readouts of the assay strip of FIG. 1.

Accordingly, there are several sample readouts as depicted in FIG. 2: (i) red lines (black in FIG. 2) in first and/or second test zones (11, 21) and respective first and/or second control zones (12, 22) indicate the assay works, and analyte is detected (FIG. 2: strip 1-3). The first three readouts in FIG. 2 show the examples with samples positive for MRSA and MSSA (strip 1), positive for MSSA only (strip 2), and positive for MRSA only (strip 3), respectively. (ii) A red line in both control zones only indicates the assay works, but no analyte is detected, meaning that the sample is negative for MSSA and MRSA (strip 4). However, this usually does not occur because samples negative for *S. aureus* would be omitted beforehand. (iii) A red line in only one of the control zones means the assay is not working properly (strip 5 and 6). (iv) A red line in a test zone only without a red line in the respective control zone suggests either the first or second detector antibody is saturated due to very high first or second analyte concentration or the assay is not working properly (this option is not shown in FIG. 2). In the case of saturation the sample may be diluted and the assay may be run again. If the first detector antibody is saturated incomplete depletion of MRSA may happen and the MSSA signal of the second test zone may be in fact due to MRSA. Typically the concentration of antibodies with respect to the concentration of *S. aureus* in the sample is chosen in a range not to obtain saturation of the antibodies. (iv) No red lines at all means the assay is not working properly (strip 7).

Colorimetric Quantification

The intensity of the red test line correlates positively to increasing bacterial concentrations. One possibility to quantify the concentration of MRSA/MSSA is a portable colorimeter without a CCD camera device that reads Au nanoparticle colour intensity (Ref 17). The instrument consists of light emitting diodes (LED), photodiode, a Logarithmic integrated chip, power source, LM324 quad operational amplifier, and capacitors. The LEDs are the light source. Photodiodes are specific for 400 nm to 550 nm from EPIGAP-EPD-470-5/0.5. The logarithmic integrated chip LOG102AID takes a logarithmic measure of reflected light. The reader displays the concentration bar on the LED with 5 levels. The reader captures the voltage changes induced by the colour reflection at the test and control lines. The relative differences in voltage between the control and test line are measured to minimize reading variations and ensure proper functioning of the instrument.

REFERENCE SIGNS

1 assay strip
2 support
3 sample application pad
4, 4' nitrocellulose membrane
5 absorption pad
10 first conjugation pad
11 first test line (spotted on nitrocellulose membrane)
12 first control line (spotted on nitrocellulose membrane)
20 second conjugation pad
21 second test line (spotted on nitrocellulose membrane)
22 second control line (spotted on nitrocellulose membrane)

CITATION REFERENCES

Ref 1 D. Mertz. Exclusive *Staphylococcus* throat carriage—at risk populations. Arch Intern Med, 169 (2009), pp. 172-178

Ref 2 P.-Y. Levy et al. Relation between nasal carriage of *Staphylococcus aureus* and surgical site infection in orthopedic surgery: The role of nasal contamination. A systematic literature review and meta-analysis. Orthopaedics & Traumatology: Surgery & Research. Volume 99, Issue 6, October 2013, Pages 645-651

Ref 3 H. Honda et al. *Staphylococcus aureus* nasal colonization and subsequent infection in intensive care unit patients: does methicillin resistance matter? Infect Control Hosp Epidemiol. 2010 June; 31(6):584-91.

Ref 4 Kavanagh et al. The use of surveillance and preventative measures for methicillin-resistant *Staphylococcus* aureus infections in surgical patients. Antimicrobial Resistance and Infection Control. 2014, 3:18

Ref 5 Young P Y et al. Surgical site infections. Surg Clin North Am. 2014 December; 94(6):1245-64.

Ref 6 L. G. M. Bode et al. 2010 Preventing Surgical-Site Infections in Nasal Carriers of *Staphylococcus aureus* N. Engl. J. Med. 362(1) 9-17

Ref 7 Yamada K et al., Detection of Methicillin-Resistant *Staphylococcus aureus* Using a Specific Anti-PBP2a Chicken IgY Antibody. Jpn. J. Infect. Dis., 66, 103-108, 2013

Ref 8 Irina Smolina, Nancy S Miller, and Maxim D Frank-Kamenetskii. Artif DNA PNA XNA. 2010 October-December; 1(2): 76-82. doi: 10.4161/adna.1.2.13256 PMCID: PMC3116573 PNA-based microbial pathogen identification and resistance marker detection. An accurate, isothermal rapid assay based on genome-specific features.

Ref 9 Lawrence Y. L. Lee, Magnus Hook, David Haviland, Rick A. Wetsel, Edward O. Yonter, Peter Syribeys, John Vernachio, and Eric L. Brown. Inhibition of Complement Activation by a Secreted *Staphylococcus aureus* Protein. The Journal of Infectious Diseases 2004; 190:571-9

Ref 10 Brian F. King And Brian J. Wilkinson. Binding of Human Immunoglobulin G to Protein A in Encapsulated *Staphylococcus aureus*. Infection and Immunity, 1981; 33 (3):666-672

Ref 11 Daniel Lim and Natalie C. Strynadka. Structural basis for the beta-lactam resistance of PBP2a from methicillin-resistant *Staphylococcus aureus*. Nature structural biology, 2002; 9 (11):870-876

Ref 12 Dirk-Jan Scheffers and Mariana G. Pinho. Bacterial Cell Wall Synthesis: New Insights from Localization Studies. Microbiology and Molecular Biology Reviews 2005; 69 (4):585-607

Ref 13 Mariana G. Pinho, Hermínia de Lencastre, and Alexander Tomasz. An acquired and a native penicillin-binding protein cooperate in building the cell wall of drug-resistant staphylococci. PNAS 2001; 98 (19) 10886-10891

Ref 14 Hidehito Matsui, Hideaki Hanaki, Megumi Inoue, Hiroyuki Akama, Taiji Nakae, Keisuke Sunakawa, and Satoshi Omura. Development of an Immunochromatographic Strip for Simple Detection of Penicillin-Binding Protein 2'. Clinical and Vaccine Immunology 2011; 18(2): 248-253

Ref 15 Mariana G. Pinho and Jeff Errington. Recruitment of penicillin-binding protein PBP2 to the division site of *Staphylococcus aureus* is dependent on its transpeptidation substrates. Molecular Microbiology 2005; 55 (3) 799-807

Ref 16 Mariana G. Pinho and Jeff Errington. Dispersed mode of *Staphylococcus aureus* cell wall synthesis in the absence of the division machinery. Molecular Microbiology 2003; 50(3):871-881

Ref 17 Paper based point-of-care testing disc for multiplex whole cell bacteria analysis (Using the immuno-disc, the presence of *S. aureus* and *P. aeruginosa* can be identified by the color change in the testing region within 5 min of sample application onto the disc). Chen-zhong Li, Katherine Vandenberga, Shradha Prabhulkara, Xuena Zhua, Lisa Schneperb, Kalai Metheeb, Charles J. Rosserd, Eugenio Almeidec. Biosensors and Bioelectronics 2011; 26:4342-4348

Ref 18 Parul A. Patel, Nathan A. Ledeboer, Christine C. Ginocchio, Susan Condon, Stephanie Bouchard, Peibing Qin, Tobi Karchmer, and Lance R. Peterson. Performance of the BD GeneOhm MRSA Achromopeptidase Assay for Real-Time PCR Detection of Methicillin-Resistant *Staphylococcus aureus* in Nasal Specimens. J Clin Microbiol 2011 49(6):2266-2268.

Ref 19 Gleb Pishchany, Susan E. Dickey, and Eric P. Skaar. Transport Components IsdA and IsdB Infection and Immunity 2009; 77(7):2624-2634

Ref 20 Santhana Raj L., Hing H. L., Baharudin Omar, Teh Hamidah Z., Aida Suhana R., Nor Asiha C. P., Vimala B., Paramsarvaran S., Sumarni G. and Hanjeet K. Rapid Method For Transmission Electron Microscope Study Of *Staphylococcus aureus* ATCC 25923. Annals of Microscopy 2007; 7:102.

Ref 21 D. A. Mecarthy, Marion G. Macey, Mary R. Cahill, and A. C. Newland. Effect of Fixation on Quantification of the Expression of Leucocyte Function-Associated Surface Antigens. Cytometry 1994; 17:39-49

Ref 22 Daniel Pirici, Laurentiu Mogoanta, Samir Kumar-Singh, Ionica Pirici, Claudiu Margaritescu, Cristina Simionescu, and Radu Stanescu. Journal of Histochemistry & Cytochemistry. Antibody Elution Method for Multiple Immunohistochemistry on Primary Antibodies Raised in the Same Species and of the Same Subtype. 2009; 57(6):567-575

Ref 23 Baochong Gao, Theresa M. Curtis, Frank A. Blumenstock, Fred L. Minnear and Thomas M. Saba. Increased recycling of a5b1 integrins by lung endothelial cells in response to tumor necrosis factor. Journal of Cell Science, 2000; (113):247-257

Ref 24 Geraint J. Parfitt, Yilu Xie, Korey M. Reid, Xavier Dervillez, Donald J. Brown, James V. Jester. A Novel Immunofluorescent Computed Tomography (ICT) Method to Localise and Quantify Multiple Antigens in Large Tissue Volumes at High Resolution. PLOS ONE 2012; 7(12):e53245

Ref 25 Eric L. Brown, Yasuhiro Nishiyama, Jesse W. Dunkle, Shreya Aggarwal, Stephanie Planque, Kenji Watanabe, Keri Csencsits-Smith, M. Gabriela Bowden, Sheldon L. Kaplan, and Sudhir Paul. Constitutive Production of Catalytic Antibodies to a *Staphylococcus aureus* Virulence Factor and Effect of Infection. Journal of Biological Chemistry 2012; 287(13):9940-9951

Ref 26 http://www.did.it/contenuti/Ibm/biblio/Evaluation%20of%20ESwab%20for%20maintaining%20viability%20of%20anaerobe.pdf

The invention claimed is:

1. A method for detecting presence or absence of a first analyte and of a second analyte in a sample, wherein the two analytes are identical except that only the first analyte has a unique antigen or epitope, the method comprising an assay including in the following order the steps of:
   a) conjugating a first detector reagent to the first analyte in order to tag the first analyte with a first detector tag;
   b) conjugating a first capture reagent to the unique antigen or epitope of the first analyte in order to capture the first analyte and to completely deplete the first analyte from the sample;
   c) conjugating a second detector reagent to the second analyte in the sample completely depleted of the first analyte in order to tag the second analyte with a second detector tag;
   d) conjugating a second capture reagent to the second analyte in order to capture the second analyte from the sample completely depleted of the first analyte;
   e) detecting the presence or absence of the first and second detector tag at the site of the first and second capture reagent, respectively, and thereby detecting the presence or absence of the first analyte and of the second analyte in the sample.

2. The method according to claim 1, wherein the first and second detector reagents are free first and second detector reagents free to move in or with the sample, and the first and second capture reagents are immobilized first and second capture reagents each immobilized at a predefined site on a substrate.

3. The method according to claim 1, wherein the concentration of the first capture reagent is equal or higher than the concentration of the first detector reagent.

4. The method according to claim 1, wherein the method is a lateral flow immunochromatography assay, using a lateral flow assay strip comprising in sample flow direction a sample application pad, a first conjugation pad, a nitrocellulose membrane with at least one first test line and optionally at least one first control line, a second conjugation pad, a nitrocellulose membrane with at least one second test line and optionally at least one second control line, and an absorption pad; the first conjugation pad containing the first detector reagent, the first test line formed by the first capture reagent, the second conjugation pad containing the second detector reagent, and the second test line formed by the second capture reagent, the optional at least one first control line contains a first control reagent which specifically binds the first detector reagent, the optional at least one second control line contains a second control reagent, which specifically binds the second detector reagent.

5. The method according to claim 1, wherein the first analyte is methicillin-resistant *Staphylococcus aureus* (MRSA) and the second analyte is methicillin-susceptible *Staphylococcus aureus* (MSSA).

6. The method according to claim 5, wherein before performing the assay the sample is pre-treated by isolating and enriching *Staphylococcus aureus* using Ig G antibody coated magnetic beads, said Ig G antibody being bound with a Fab region to the magnetic bead leaving a Fc region free to specifically interact with protein A of *Staphylococcus aureus*.

7. The method according to claim 1, wherein the first detector reagent and the first capture reagent are specific for distinct epitopes of penicillin binding protein 2a (PBP2a); and the second detector reagent and the second capture reagent are specific for distinct epitopes of penicillin binding protein 2 (PBP2).

8. The method according to claim 1, wherein the sample is collected from a biological, environmental or food specimen.

9. The method according to claim 1, wherein the first detector reagent is an antibody and the first capture reagent is an antibody.

10. The method according to claim 9, wherein the second detector reagent is an antibody and the second capture reagent is an antibody.

11. The method according to claim 1, wherein the ratio of the concentration of the first capture reagent and the concentration of the first detector reagent is between 1:1 and 5:1.

12. The method according to claim 1, wherein the ratio of the concentration of the first capture reagent and the concentration of the first detector reagent is between 1.5:1 and 3:1.

13. A lateral flow immunochromatography strip for performing the method according to claim 1 in order to detect a first analyte and a second analyte, wherein the two analytes are identical except that only the first analyte has a unique antigen or epitope, comprising in sample flow direction a sample application pad, a first conjugation pad, a nitrocellulose membrane with at least one first test line and optionally at least one first control line, a second conjugation pad, a nitrocellulose membrane with at least one second test line and optionally at least one second control line, and an absorption pad;

the first conjugation pad containing a first detector reagent to the first analyte in order to tag the first analyte with a first detector tag;

the at least one first test line being formed by a first capture reagent to the unique antigen or epitope of the first analyte in order to capture the first analyte and to completely deplete the first analyte from the sample;

the second conjugation pad containing a second detector reagent to the second analyte in the sample completely depleted of the first analyte in order to tag the second analyte with a second detector tag;

the at least one second test line being formed by a second capture reagent to the second analyte in order to capture the second analyte from the sample completely depleted of the first analyte;

the optional at least one first control line contains a first control reagent which specifically binds the first detector reagent;

the optional at least one second control line contains a second control reagent, which specifically binds the second detector reagent.

14. The lateral flow immunochromatography strip according to claim 13, wherein the first and second detector reagents are free first and second detector reagents free to move in or with the sample, and the first and second capture reagents are immobilized first and second capture reagents immobilized at the site of the first and second test line respectively, and wherein the reagents of the optional first and second control lines are immobilized at the site of the first and second control line.

15. The lateral flow immunochromatography strip according to claim 13, wherein the first analyte is methicillin-resistant *Staphylococcus aureus* (MRSA) and the second analyte is a methicillin-susceptible *Staphylococcus aureus* (MS SA).

16. The lateral flow immunochromatography strip according to claim 13, wherein the first detector reagent and the first capture reagent are specific for distinct epitopes of penicillin binding protein 2a (PBP2a); and the second detector reagent and the second capture reagent are specific for distinct epitopes of penicillin binding protein 2 (PBP2).

17. The lateral flow immunochromatography strip according to claim 13, wherein at least one further set of first conjugation pad and first test line follows a first set of first conjugation zone and first test line.

18. A kit for detecting the presence or absence of a first analyte and of a second analyte in a sample, the kit comprising: a lateral flow immunochromatography strip according to claim 13.

19. The kit according to claim 18, further comprising at least one of the following:

a swab for taking a sample from a patient, including agents to elute the sample from the swab;

an extracellular fibrinogen-binding protein (Efb) immunochromatography dipstick to detect the absence or presence of *S. aureus* in a sample;

Ig G antibody coated magnetic beads to isolate and enrich *Staphylococcus aureus*, said Ig G antibody being bound with its Fab region to the magnetic bead leaving its Fc region free to specifically interact with protein A of

*Staphylococcus aureus*; including agents for washing steps and eluting *Staphylococcus aureus* from the magnetic beads; and
an agent for fixation and permeabilization of *S. aureus*.

\* \* \* \* \*